United States Patent [19]

Olah

[11] Patent Number: 4,737,594

[45] Date of Patent: Apr. 12, 1988

[54] PROCESS FOR THE MANUFACTURE OF VINYL CHLORIDE

[75] Inventor: George A. Olah, Beverly Hills, Calif.

[73] Assignee: Produits Chimiques Ugine Kuhlmann, France

[21] Appl. No.: 511,516

[22] Filed: Jul. 6, 1983

[30] Foreign Application Priority Data

Jul. 6, 1982 [FR] France ................ 82 11810

[51] Int. Cl.$^4$ .............................. C07C 13/74
[52] U.S. Cl. .................................. 570/222
[58] Field of Search ...................... 570/222, 255

[56] References Cited

U.S. PATENT DOCUMENTS

| | | | |
|---|---|---|---|
| 1,422,838 | 7/1922 | Curme | 570/255 |
| 3,055,955 | 9/1962 | Hodges | 570/222 |
| 3,702,311 | 11/1972 | Beard | 570/222 |
| 3,983,180 | 9/1976 | Habata et al. | 570/258 |
| 3,987,119 | 10/1976 | Kurtz et al. | 570/223 |
| 4,020,117 | 4/1977 | Sisson | 570/243 |
| 4,373,109 | 2/1983 | Olah | 585/640 |

FOREIGN PATENT DOCUMENTS

WO00859 3/1983 PCT Int'l Appl. ............. 570/255

*Primary Examiner*—J. E. Evans
*Attorney, Agent, or Firm*—Sigalos & Levine

[57] ABSTRACT

A process for the manufacture of vinyl chloride by the condensation of methyl chloride, obtained from methane or from methanol, followed by an oxychlorination of the condensation products and then by a dehydrochlorination.

The condensation of methyl chloride preferably takes place in the presence of a catalyst selected from an aluminosilicate or an oxide, oxyhalide or sulfide of a transition metal of Groups IV, V, VI and VII of the Periodic Table.

10 Claims, No Drawings

PROCESS FOR THE MANUFACTURE OF VINYL CHLORIDE

BACKGROUND OF THE INVENTION

The present invention concerns a process for the manufacture of vinyl chloride from methyl chloride.

Vinyl chloride, whose production has been widely developed during the course of the last thirty years, essentially serves as a monomer, as a base product for the manufacture of chlorinated vinyl resins.

Originally, the vinyl chloride monomer was manufactured by the addition of hydrochloric acid onto acetylene. This process has now been replaced by the chlorination or oxychlorination of ethylene, with thermal dehydrochlorination of the products obtained. These products are widely described in the literature, as for example in "Industrial Organic Chemistry" by K. Weissermel and H. J. Arpe, Verlag Chemie, Weinheim, New York 1978.

The present manufacturing methods, based on ethylene, are dependent on petrochemical sources, in particular on naphtha or on the cracking products of light hydrocarbons.

SUMMARY OF THE INVENTION

The process according to the invention makes it possible to manufacture vinyl chloride directly from methyl chloride; methyl chloride being customarily obtained from methane or from methanol.

Briefly stated, the invention comprises a process for the manufacture of vinyl chloride comprising chlorinating methane or methanol to form methyl chloride, catalytically condensing said methyl chloride, oxychlorinating said condensation product, and dehydrochlorinating said oxychlorinated product to form vinyl in the following manner:

DETAILED DESCRIPTION

The process can be schematized overall into three stages in the following manner:

1. $2CH_3Cl \longrightarrow$ condensation product $+ HCl$

2. Condensation products $+ HCl + 1/2 O_2 \xrightarrow{\text{oxychlorination}}$ $ClCH_2CH_2Cl + H_2O$ 3. $ClCH_2CH_2Cl \xrightarrow{\text{dehydrochlorination}} CH_2 = CHCl + HCl$ The hydrochloric acid of the third stage can be recovered an recycled at the oxychlorination of the condensation products or at the chlorination of the methanol into methyl chloride:

$$CH_3OH + HCl \rightarrow CH_3Cl + H_2O$$

The hydrochloric acid can also be recycled for use in the oxychlorination of the methane:

$$CH_4 + HCl + \tfrac{1}{2}O_2 \rightarrow CH_3Cl + H_2O$$

Depending upon the nature of the raw material used, the overall reaction can be symbolized by one of the two following equations:

$$2 CH_3OH + HCl + \tfrac{1}{2}O_2 \Rightarrow CH_2=CHCl + 3 H_2O$$
$$4 CH_4 + CL_2 + 2.5 O_2 \Rightarrow 2 CH_2=CHCL + 5 H_2O$$

The condensation according to the first stage is a known chemical reaction, as disclosed in U.S. Pat. No. 4,373,109 and particularly satisfactory results (namely a decrease in secondary reactions) are obtained when it is carried out in the presence of an acid-base bifunctional catalyst, at a temperature from 250° to 450° C. and preferably between 325° and 375° C. with an hourly spatial speed (velocity) of the gases (GHSV) of 50 to 300 or preferably between 75 to 100. The bifunctional catalysts preferred are the oxides, oxyhalides, or sulfides of the transition metals of Groups IV, V, VI and VII of the Periodic Table and particularly of tantalum, niobium, zirconium, tungsten, titanium, and chromium. They are customarily deposited on a support such as alumina, zirconium oxide, and silica and others. One can also utilize as catalysts the aluminosilicates such as the acid form of a mordenite having a Si/Al ratio of at least 10. Condensation can also take place in the presence of an inert diluent such as, for example, an excess of methane or of nitrogen.

The oxychlorination reaction customarily takes place in the presence of a copper chloride catalyst at temperatures between 200° and 300° C. and more particularly in the vicinity of 250° C. under a pressure from 1 to 10 bars.

The dehydrochlorination reaction is purely thermal. The gaseous dichloroethane is transformed into vinyl chloride by passing into a reactor at a temperature of 400° to 530° C. under a pressure from 5 to 20 bars. In general, about 50% of the dichloroethane is transformed into vinyl chloride, with the unreacted dichloroethane being recycled.

The methyl chloride can come from the chlorination of methanol or of methane.

An advantageous process for obtaining methyl chloride consists in having hydrochloric acid react with the methanol, and more particularly the hydrochloric acid formed as a by-product of the third stage described above. The reaction can take place in the liquid phase between 180° and 240° C. in the presence of a catalyst customarily based on $ZnCl_2$ under a pressure of 1 to 5 bars. The molar ratio of $HCl/CH_3OH$ is preferably between 1.1 and 1.3. This reaction can likewise be carried out in the vapor phase at a temperature between 400 and 450° C. in the presence of alumina as catalyst.

Such a process makes it possible to produce vinyl chloride directly and continuously from methanol by passing through the intermediate stage of methyl chloride according to the following equations:

$$2CH_3OH + 2HCl \longrightarrow 2CH_3Cl + 2H_2O$$

$$2CH_3Cl \xrightarrow[\text{then } \tfrac{1}{2}O_2]{\text{condensation}} ClCH_2CH_2Cl + H_2O$$

$$ClCH_2CH_2Cl \longrightarrow CH_2 = CHCl + HCl$$

A similar technique can be envisioned starting from methane:

$$CH_4 + Cl \longrightarrow CH_3Cl + HCl$$

$$3CH_4 + 3HCl + 3/2O_2 \quad 3CH_3Cl + 3H_2O$$

-continued

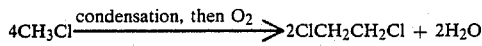

The chlorination of the methane can be carried out at a temperature between 400° and 450° C. under a slight pressure. Methyl chloride can also be obtained by photochemistry. These processes for obtaining methyl chloride have been described, for example, by: F. Asinger "Paraffin Chemistry and Technology" Pergamon Press, New York, 1968; M. L. Poutsma "Methods in Free Radical Chemistry", Vol II; E. S. Huyser, Ed., M. Dekker, New York 1969; and R. Weissermel and H. J. Arpe "Industrial Organic Chemistry" Verlag Chemie 1978, pp. 46–47.

Another process consists of an ionic or noble metal promoted chlorination of the methane taking place at a temperature between 100° and 325° C. and more particularly between 200° and 300° C. in the presence of a catalyst selected from among the halides or oxyhalides of the metals of groups IV, V, VI of the Periodic Table, as for example, tantalum, tungsten, titanium, chromium and others, or also from among the metallic catalysts of group VIII; such as platinum or palladium. This type of catalyst is preferably deposited on an appropriate support such as alumina or graphite. One can also use the catalysts of the Bronstead type such as perfluorinated sulfonic acids or sulfonic acid resins. This ionic chlorination is illustrated in U.S. patent application Ser. No. 298,390.

Generally speaking, the molar ratio of $Cl_2/CH_4$ is customarily between 1 and 5 and more precisely between 1.5 and 3. The following examples serve to further illustrate the invention, with the given compositions being adjusted in order to furnish a total conversion rate (degree of conversion) of 100%.

EXAMPLE 1

Methane and chlorine in a ratio of 3/1 respectively pass into a tubular reactor at a temperature of 235° C. on a catalyst composed of 10% by weight of tantalum oxyfluoride deposited onto 90% by weight of alumina. The GHSV is about 50.

The reaction product, other than the excess methane, contains 96.5% of methyl chloride and 3.5% of ethyl chloride, as well as the corresponding hydrochloric acid. This reaction product, without separation, is passed across a second reactor onto a catalyst composed of 20% tungsten oxide supported by 80% alumina. The GHSV is about 80 with the gaseous mixture passing the catalyst at a temperature of 365° C.

From the product of the condensation stage, one extracts the methane as well as the unreacted methyl chloride not yet having reacted, which is recycled. The fraction containing the condensation product, including anhydrous hydrochloric acid, is set to react with oxygen in the presence of $CuCl_2$ as catalyst under a pressure of 2 to 3 atmospheres at a temperature of 220° –240° C. The 1,2 dichloroethane obtained with a yield of 95% and a selectivity of 98%, is dehydrochlorinated thermically at 500° C.

The vinyl chloride is obtained with 98% of selectivity based on the dichloroethane. The hydrochloric acid formed as a by-product is recycled for use in the oxychlorination.

EXAMPLE 2

Methyl alcohol and hydrochloric acid are reacted at 320° –370° C. in stoichiometrical quantities, in the presence of alumina as the catalyst. The reaction product containing methyl chloride, without separation, is directly sent into a condensation reactor, with the conditions of condensation, oxychlorination and dehydrochlorination remaining identical to those of Example 1.

EXAMPLE 3

The conditions of Example 1 are used with the catalyst based on tantalum oxyfluoride being replaced by 0.5% of palladium deposited on 99.5% of alumina and the catalyst based on tungsten oxide of the condensation stage being replaced by the acid form of mordenite. There is obtained vinyl chloride with 99% of selectivity based on the dichloroethane.

While the invention has been described in connection with a preferred embodiment, it is not intended to limit the scope of the invention to the particular form set forth, but, on the contrary, it is intended to cover such alternatives, modifications and equivalents as may be included within the spirit and scope of the invention as defined by the appended claims.

What is claimed is:

1. A process for the manufacture of vinyl chloride comprising directly and continously chlorinating methane or methanol to form methyl chloride, catalytically condensing said methyl chloride, oxychlorinating said condensation product, and dehydrochlorinating said oxychlorinated product to form vinyl chloride.

2. The process of claim 1, wherein the methyl chloride condensation takes place in the presence of a catalyst selected from aluminosilicates or an oxide, oxyhalide or sulfide of a transition metal of Group IV, V, VI and VII of the Periodic Table for a time and at a temperature sufficient to achieve condensation 3. The process of claim 1 or 2, wherein the methyl chloride condensation takes place in the presence of an inert diluent.

4. The process of claims 1 or 2 wherein the oxychlorination reaction takes place in the presence of a copper chloride catalyst for a time and at a temperature sufficient to form dichloroethane.

5. The process of claims 1 or 2 wherein the dichloroethane is thermally dehydrochlorinated to form vinyl chloride.

6. The process of claims 1 or 2 wherein hydrochloric acid formed during the dehydrochlorination stage is recycled for use in the oxychlorination of the condensation products.

7. The process of claims 1 or 2 wherein the hydrochloric acid formed during the dehydrochlorination stage is recycled for use in the chlorination of methane or methanol into methyl chloride.

8. A process for the direct and continuous manufacture of vinyl chloride comprising chlorinating methane or methanol to form methyl chloride, condensing said methyl chloride in the presence of an acid-base bifunctional catalyst at a temperature of from about 250° to 450° C., to form a condensation product and hydrochloric acid, oxychlorinating said condensation product with a source of oxygen and hydrochloric acid in the presence of a copper chloride catalyst to form dichloroethane, and thermally dehydrochlorinating said dichloroethane at a temperature of from about 400° to 530° C., under a pressure of from about 5 to 20 bars to form vinyl chloride.

9. The process of claim 8 wherein the hydrochloric acid formed during the dehydrochlorination of dichloroethane is recycled for use in the chlorination, or oxychlorination of the condensation product, or both.

10. The process of claim 9, wherein the vinyl chloride is continuously produced from methanol or methane by recycling the hydrochloric acid formed as a by-product in the dehydrochlorination to chlorinate the methanol or methane.

* * * * *

UNITED STATES PATENT AND TRADEMARK OFFICE
CERTIFICATE OF CORRECTION

PATENT NO. : 4,737,594
DATED : April 12, 1988
INVENTOR(S) : Olah

It is certified that error appears in the above-identified patent and that said Letters Patent are hereby corrected as shown below:

Col. 2, line 1, cancel the numeral "4" at the end of that line;

Col. 2, line 2, insert the numeral --4-- before "$CH_4$";

Col. 2, line 45, "$HCl/CH_3OH$" should read --$HCl/CH_3OH$--;

Column 2, line 68, please insert -- $\longrightarrow$ -- between "$3/2O_2$ and the $3CH_3Cl$";

Column 3, line 63, "220° -240°C" should read --220° - 240°C--; and

Column 4, line 6, "320° -370°C" should read --320° - 370°C--.

Signed and Sealed this

Twentieth Day of September, 1988

Attest:

DONALD J. QUIGG

Attesting Officer     Commissioner of Patents and Trademarks